United States Patent [19]

Hayashi et al.

[11] 4,234,597
[45] Nov. 18, 1980

[54] 6,9-NITRILO(IMINO)-PROSTAGLANDIN ANALOGUES

[75] Inventors: Masaki Hayashi, Takatsuki; Shuichi Ohuchida, Kyoto; Yoshinobu Arai, Toyonaka, all of Japan

[73] Assignee: Ono Pharmaceutical Co. Ltd., Osaka, Japan

[21] Appl. No.: 20,339

[22] Filed: Mar. 14, 1979

[30] Foreign Application Priority Data

Mar. 18, 1978 [JP] Japan .................. 53-030531

[51] Int. Cl.³ .................. A61K 31/40; C07D 209/52
[52] U.S. Cl. .................. 424/274; 260/326.27; 542/429
[58] Field of Search .................. 260/326.27; 424/274; 542/429

[56] References Cited

U.S. PATENT DOCUMENTS

| | | | |
|---|---|---|---|
| 4,097,489 | 6/1978 | Bundy | 260/326.27 |
| 4,151,176 | 4/1979 | Bundy | 260/326.27 |
| 4,152,514 | 5/1979 | Bundy | 542/429 |
| 4,161,584 | 7/1979 | Bundy | 542/429 |
| 4,178,367 | 12/1979 | Masaki et al. | 542/429 |

Primary Examiner—Mary C. Lee
Attorney, Agent, or Firm—Stevens, Davis, Miller & Mosher

[57] ABSTRACT

Prostaglandin I₂ analogues of the formula:

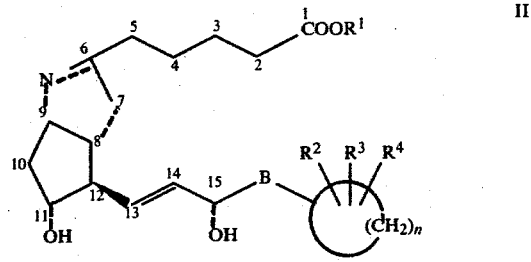

[wherein $R^1$ represents hydrogen, alkyl of 1 to 12 carbon atoms, aralkyl of 7 to 12 carbon atoms, cycloalkyl of 4 to 7 carbon atoms optionally substituted by alkyl of 1 to 4 carbon atoms, phenyl optionally substituted by chlorine, trifluoromethyl, alkyl of 1 to 4 carbon atoms or phenyl, or represents a group $-C_pH_{2p}COOR^5$, $-C_qH_{2q}OR^6$ or

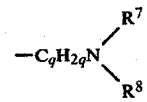

(wherein $R^5$, $R^7$ and $R^8$ represent alkyl of 1 to 4 carbon atoms, $R^6$ represents hydrogen or alkyl of 1 to 4 carbon atoms, p represents an integer of from 1 to 12, and q represents an integer of from 2 to 12), $R^2$, $R^3$ and $R^4$, represent hydrogen or alkyl of 1 to 8 carbon atoms, B represents a single bond, or alkylene of 1 to 4 carbon atoms, n represents 3, 4, 5 or 6, and the symbol ≅ represents a single or double bond] and, when appropriate, non-toxic salts, including acid addition salts, thereof are new compounds possessing pharmacological properties typical of the prostaglandins.

20 Claims, No Drawings

6,9-NITRILO(IMINO)-PROSTAGLANDIN ANALOGUES

DESCRIPTION
"6,9-NITRILO(IMINO)-PROSTAGLANDIN ANALOGUES"

This invention relates to new prostaglandin I₂ (PGI₂) analogues, to a process for their preparation and pharmaceutical compositions containing them.

PGI₂ is a physiologically active substance having the following formula:

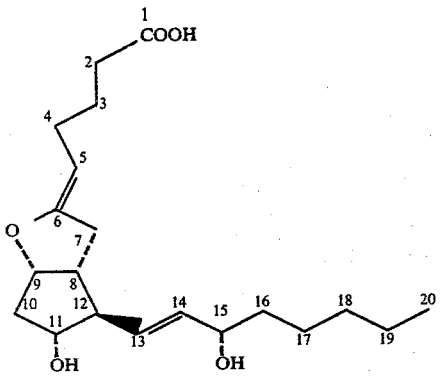

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI₂ can be prepared by incubation of prostaglandin G₂ (PGG₂) or prostaglandin H₂ (PGH₂) with microsomal fractions prepared from thoracic aorta of swine, mesenteric artery of swine, rabbit aorta or the stomach fundus of rats. PGI₂ has a relaxing activity on the artery, which is peculiar to the artery and which does not operate on other smooth muscle. Furthermore, PGI₂ strongly inhibits arachidonic acid-induced blood platelet aggregation of the human.

Taking into consideration that thromboxane A₂ prepared by incubation of PGG₂ or PGH₂ with blood platelet microsome has a contracting activity on the artery and an aggregating activity on blood platelets, the properties of PGI₂ heretofore mentioned show that PGI₂ fulfils a very important physiological part in a living body. PGI₂ may be useful in the treatment of arteriosclerosis, cardiac failure or thrombosis.

Widespread investigations have been carried out in order to discover inter alia new products possessing the pharmacological properties of the 'natural' PGI₂, or one or more of such properties to an enhanced degree, or hitherto unknown pharmacological properties. As a result of extensive research and experimentation it has been discovered that by replacing the 6,9-epoxy group (i.e. —O—) by a group =N—, in which the double bond is attached to the 6-position (hereinafter referred to as a 6,9-nitrilo group), or by a group —NH— (hereinafter referred to as a 6,9-imino group), and by replacing the pentyl group at the end of the aliphatic group linked to the 12-position of the aliphatic ring of PGI₂ by a cycloalkyl group or an alkyl group substituted by a cycloalkyl group, the pharmacological properties of the 'natural' PGI₂ are, in some aspects of its activities, improved or modified.

The present invention accordingly provides new prostaglandin I₂ analogues of the general formula:

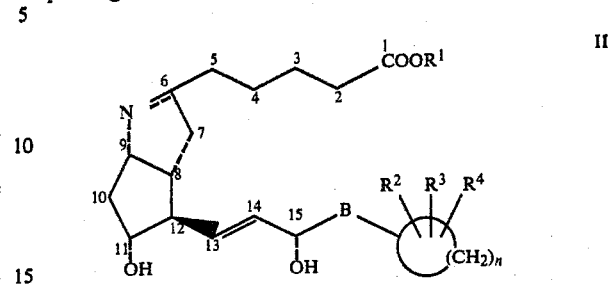

[wherein $R^1$ represents a hydrogen atom, a straight- or branched-chain alkyl group containing from 1 to 12 carbon atoms, an aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one substituent selected from the chlorine atom, the trifluoromethyl group, straight- or branched-chain alkyl groups containing from 1 to 4 carbon atoms and the phenyl group or represents a group $-C_pH_{2p}COOR^5$, $-C_qH_{2q}OR^6$ or $$-C_qH_{2q}N\begin{matrix}R^7\\R^8\end{matrix}$$

(wherein $R^5$, $R^7$ and $R^8$, which may be the same or different, each represent a straight- or branched-chain alkyl group containing from 1 to 4 carbon atoms, $R^6$ represents a hydrogen atom or a straight- or branched-chain alkyl group containing from 1 to 4 carbon atoms, p represents an integer of from 1 to 12, and q represents an integer of from 2 to 12), $R^2$, $R^3$ and $R^4$, which may be the same or different, each represent a hydrogen atom or a straight- or branched-chain alkyl group containing from 1 to 8 carbon atoms, B represents a single bond, or a straight- or branched-chain alkylene group containing from 1 to 4 carbon atoms, n represents 3, 4, 5 or 6, the symbol ≡≡≡ attached to the C₆ carbon atom represents a single or double bond, the double bond between C₁₃–C₁₄ is trans (i.e. E), and the hydroxy groups attached to the C₁₁ and C₁₅ carbon atoms of formula II are in α-configuration] and non-toxic acid addition salts thereof and, when $R^1$ represents a hydrogen atom, non-toxic (e.g. sodium) salts thereof. It will be appreciated that acid addition salt formation may take place with a 6,9-nitrilo or 6,9-imino group; acid addition salt formation is also possible with a group

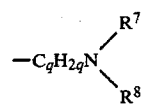

within the definition of the symbol $R^1$, in which q, $R^7$ and $R^8$ are as hereinbefore defined.

Preferred compounds of formula II are those wherein $R^1$ represents a hydrogen atom or a straight- or branched-chain alkyl group containing from 1 to 12 carbon atoms, more preferably from 1 to 4 carbon atoms, especially methyl, B preferably represents a single bond or a methylene group. One of $R^2$, $R^3$ and $R^4$ preferably represents an alkyl group containing from 1 to 4 carbon atoms and the other two represent hydrogen atoms, and n is preferably 4 or 5.

It is to be understood that the structure

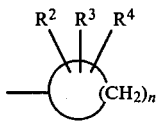

in general formula II and in subsequent formulae appearing in this specification represents an optionally substituted cyclobutyl, cyclopentyl, cyclohexyl or cycloheptyl group, and that one of the substituents $R^2$, $R^3$ and $R^4$ may be attached to the carbon atom by which the cycloalkyl group is attached to the symbol B.

The present invention is concerned with all compounds of general formula II in the optically active 'natural' form or its enantiomeric form, or mixtures thereof, more particularly the racemic form, consisting of equimolecular mixtures of the optically active 'natural' form and its enantiomeric form.

As will be apparent to those skilled in the art, the compounds depicted in general formula II have at least five centres of chirality, these five centres of chirality being at the C-8, C-9, C-11, C-12 and C-15 carbon atoms. Still further centres of chirality may occur when $R^1$, $R^2$, $R^3$ or $R^4$ is a branched-chain alkyl group, or B or the moiety $C_pH_{2p}$ or $C_qH_{2q}$ is a branched-chain alkylene group. The presence of chirality leads as is well known to the existence of isomerism. However, the compounds of general formula II all have such a configuration that the substituent groups attached to the ring carbon atoms in positions identified as 8 and 12 are trans with respect to each other and that the substituent groups attached to the ring carbon atoms in the positions identified as 8 and 9 are cis with respect to each other. Accordingly, all isomers of general formula II, and mixtures thereof, which have those substituent groups attached to the ring carbon atoms in positions 8 and 12 in the trans-configuration, those attached in 8 and 9 in the cis-configuration and have hydroxy groups as depicted in the 11- and 15-positions are to be considered within the scope of general formula II.

Examples of the straight- or branched-chain alkyl group containing from 1 to 12 carbon atoms represented by $R^1$ are methyl, ethyl, propyl, butyl, pentyl, hexyl, heptyl, octyl, nonyl, decyl, undecyl, dodecyl and their isomers.

Examples of the aralkyl group containing from 7 to 12 carbon atoms represented by $R^1$ are benzyl, 1-phenylethyl, 2-phenylethyl, 3-phenylbutyl, 4-phenylbutyl, 1-(2-naphthyl)ethyl and 2-(1-naphthyl)ethyl.

Examples of the cycloalkyl group containing from 4 to 7 carbon atoms unsubstituted or substituted by at least one straight- or branched-chain alkyl group containing from 1 to 4 carbon atoms represented by $R^1$ are cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, 2,6-dimethyl-4-propylcyclohexyl and cycloheptyl.

Examples of the phenyl group unsubstituted or substituted by at least one substituent selected from the chlorine atom, the trifluoromethyl group, straight- or branched-chain alkyl groups containing from 1 to 4 carbon atoms and the phenyl group represented by $R^1$ are phenyl, 2-chlorophenyl, 3-chlorophenyl, 4-chlorophenyl, 2,4-dichlorophenyl, 2,4,6-trichlorophenyl, 2-tolyl, 3-tolyl, 4-tolyl, 4-ethylphenyl, 4-tert-butylphenyl, 4-sec-butylphenyl, 3-trifluoromethylphenyl and 4-biphenyl.

The straight- or branched-chain alkylene group represented by $-C_pH_{2p}-$ and $-C_qH_{2q}-$ may be methylene (when p in the $-C_pH_{2p}-$ moiety is 1), ethylene, trimethylene, tetramethylene, pentamethylene, hexamethylene, heptamethylene, octamethylene, nonamethylene, decamethylene, undecamethylene, dodecamethylene, and the isomers thereof, with straight-chain alkylene groups being preferable.

Examples of the straight- or branched-chain alkyl groups containing from 1 to 8 carbon atoms represented by $R^2$, $R^3$ and $R^4$, are methyl, ethyl, propyl, butyl, pentyl, hexyl, heptyl, octyl and the isomers thereof.

Examples of the straight- or branched-chain alkyl groups containing from 1 to 4 carbon atoms represented by $R^5$, $R^6$, $R^7$ and $R^8$ are methyl, ethyl, propyl, isopropyl, butyl, isobutyl, sec-butyl and tert-butyl.

Examples of the straight- or branched-chain alkylene group containing from 1 to 4 carbon atoms represented by B are methylene, ethylene, methylmethylene, trimethylene, 1-methylethylene, 2-methylethylene, ethylmethylene, dimethylmethylene, tetramethylene, 1-methyltrimethylene, 2-methyltrimethylene, 3-methyltrimethylene, 1,1-dimethylethylethylene, 1,2-dimethylethylene, 2,2-dimethylethylene, 1-ethylethylene, 2-ethylethylene, methylethylmethylene, propylmethylene and isopropylmethylene.

Preferably the

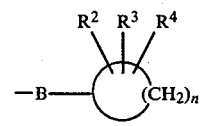

group represents cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-1-cyclohexyl)ethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl and 2-cycloheptylethyl: 3-propylcyclopentyl, 1-cyclopentylethyl, cyclohexyl, 4-ethylcyclohexyl, 4-propylcyclohexyl and 3-butylcyclopentyl are especially preferred.

Examples of suitable non-toxic acid addition salts are the salts with inorganic acids such as hydrochloric acid, hydrobromic acid, hydroiodic acid, sulphuric acid, phosphoric acid and nitric acid, and with organic acids such as acetic acid, propionic acid, lactic acid, tartaric acid, citric acid, methanesulphonic acid, ethanesulphonic acid, benzenesulphonic acid, toluenesulphonic acid, isethionic acid and succinic acid.

According to a feature of the present invention, the prostaglandin $I_2$ analogues of general formula II, wherein the symbol≡≡≡attached to the 6-position represents a double bond, and the other symbols are as hereinbefore defined, i.e. compounds of the general formula:

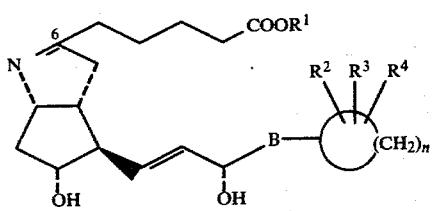

IIA (wherein the various symbols are as hereinbefore defined) are prepared by cyclisation of a compound of the general formula:

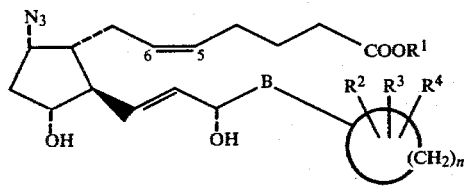

III

[wherein the double bond between $C_5$–$C_6$ is cis (i.e. Z) and the other symbols are as hereinbefore defined] in an inert organic solvent, e.g. toluene, benzene or acetonitrile, at a temperature from ambient to 110° C.

If desired, products of general formula IIA may be purified by conventional means, e.g. by thin layer or column chromatography on silica gel, to give the pure $PGI_2$ analogues.

Esters of general formula III, wherein $R^1$ is other than a hydrogen atom, and the other symbols are as hereinbefore defined, may be prepared by esterification of the corresponding acid of general formula III, wherein $R^1$ represents a hydrogen atom, and the other symbols are as hereinbefore defined, by methods known per se (i.e. methods heretofore used or described in the chemical literature), for example, when $R^1$ is an alkyl group, by reaction with (1) a diazoalkane, (2) an alkyl halide, or (3) an N,N-dimethylformamidedialkyl acetal, or when $R^1$ is an alkyl group or any other esterifying group within the definition of $R^1$, (4) using dicyclohexylcarbodiimide (by the procedure described in our Japanese Patent No. 762305), (5) using a pivaloyl halide (by the procedure described in our British Patent No. 1364125), or (6) using an arylsulphonyl or alkylsulphonyl halide (by the procedure described in our British Patent No. 1362956).

The preparation of esters using a diazoalkane is carried out by reacting the corresponding acid with an appropriate diazoalkane in an inert organic solvent, e.g. diethyl ether, ethyl acetate, methylene chloride, or acetone, or a mixture of two or more of them, at a temperature from ambient to −10° C., preferably 0° C. The preparation of estes using an alkyl halide is carried out by reacting the corresponding acid with an appropriate alkyl halide, e.g. methyl iodide, (i) in acetone in the presence of an alkali metal, e.g. potassium or sodium, carbonate [cf. J. Org. Chem., 34, 3717 (1969)], (ii) in N,N-dimethylacetamide or N,N-dimethylformamide in the presence of an alkali metal, e.g. potassium or sodium, bicarbonate [cf. Advan. Org. Chem., 5, 37 (1965)], or (iii) in dimethyl sulphoxide in the presence of calcium oxide [cf. Synthesis, 262 (1972) ], at a temperature from 0° C. to ambient. The preparation of esters using an N,N-dimethylformamide-dialkyl acetal is carried out by reacting the corresponding acid with an N,N-dimethylformamide-dialkyl acetal, e.g. N,N-dimethylformamide-dimethyl acetal, in anhydrous benzene [cf. Helv. Chem. Acta, 48, 1746 (1965)]. The preparation of esters using dicyclohexylcarbodiimide is carried out by reacting the corresponding acid with an appropriate alcohol $R^1OH$, wherein $R^1$ is other than a hydrogen atom, in an inert organic solvent such as a halogenated hydrocarbon, e.g. chloroform or methylene chloride, in the presence of a base such as pyridine or picoline, preferably pyridine, at a temperature from 0° C. to ambient. The preparation of esters using a pivaloyl, arylsulphonyl or alkylsulphonyl halide is carried out by reacting the corresponding acid with a tertiary amine, e.g. triethylamine or pyridine, and a pivaloyl halide, e.g. pivaloyl chloride, arylsulphonyl halide, e.g. p-toluenesulphonyl chloride or benzenesulphonyl chloride, or alkylsulphonyl halide, e.g. methanesulphonyl chloride or ethanesulphonyl chloride, in the presence or absence of an inert organic solvent such as a halogenated hydrocarbon, e.g. chloroform or methylene chloride, or diethyl ether, to prepare a mixed acid anhydride of the acid, and adding thereto, at a temperature from 0° C. to ambient, an alcohol $R^1OH$, wherein $R^1$ is other than a hydrogen atom, to obtain the esters.

Compounds of general formula III, wherein $R^1$ represents a hydrogen atom, or a straight- or branched-chain alkyl group containing from 1 to 4 carbon atoms, and the other symbols are as hereinbefore defined, i.e. compounds of the general formula:

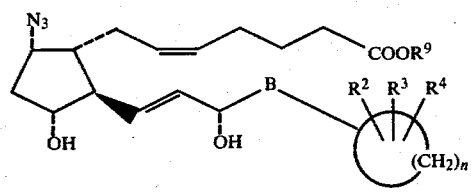

IV (wherein $R^9$ represents a hydrogen atom or a straight- or branched-chain alkyl group containing from 1 to 4 carbon atoms, and the other symbols are as hereinbefore defined) may be prepared by reaction of a compound of the general formula:

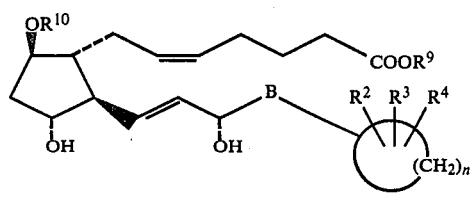

(V)

(wherein R[10] represents an alkylsulphonyl or arylsulphonyl group, and the other symbols are as hereinbefore defined) with a reagent for the replacement of the group OR[10] by the azido group, e.g. sodium azide or lithium azide, in an inert organic solvent such as dimethyl sulphoxide, N,N-dimethylformamide or N,N-dimethylacetamide, at a temperature from ambient to 110° C.

Compounds of general formula V may be prepared by the series of reactions depicted schematically below in Scheme A, wherein R[11] represents a tetrahydropyran-2-yl or tetrahydrofuran-2-yl group, each such group being unsubstituted or substituted by at least one alkyl group, or a 1-ethoxyethyl group, R[12] represents the benzoyl group, and the other symbols are as hereinbefore defined.

tetrahydrofuran, or a lower alkanol, e.g. methanol or ethanol, or with anhydrous potassium carbonate in an anhydrous lower alkanol, such as methanol, usually at ambient temperature.

Compounds of general formula IX may also be converted into compounds of general formula VIII by methods known per se for the reduction of an oxo group in the 9-position of a prostaglandin E compound to a hydroxy group, for example by means of sodium borohydride in methanol. The product is a mixture of compounds of general formula VIII and those of general formula VI, and the mixture is separated by conventional means, for example by thin layer, column or high-speed liquid chromatography on silica gel to give each isomer.

Compounds of general formula X may be prepared by sulphonylation of a compound of general formula VIII with an alkylsulphonyl halide such as methanesulphonyl chloride or ethanesulphonyl chloride, or an arylsulphonyl halide such as benzenesulphonyl chloride or p-toluenesulphonyl chloride, in an inert organic solvent such as methylene chloride in the presence of a tertiary amine such as triethylamine or pyridine, or in a basic solvent such as pyridine, at a temperature of −30° to 50° C.

The conversion of compounds of general formula X

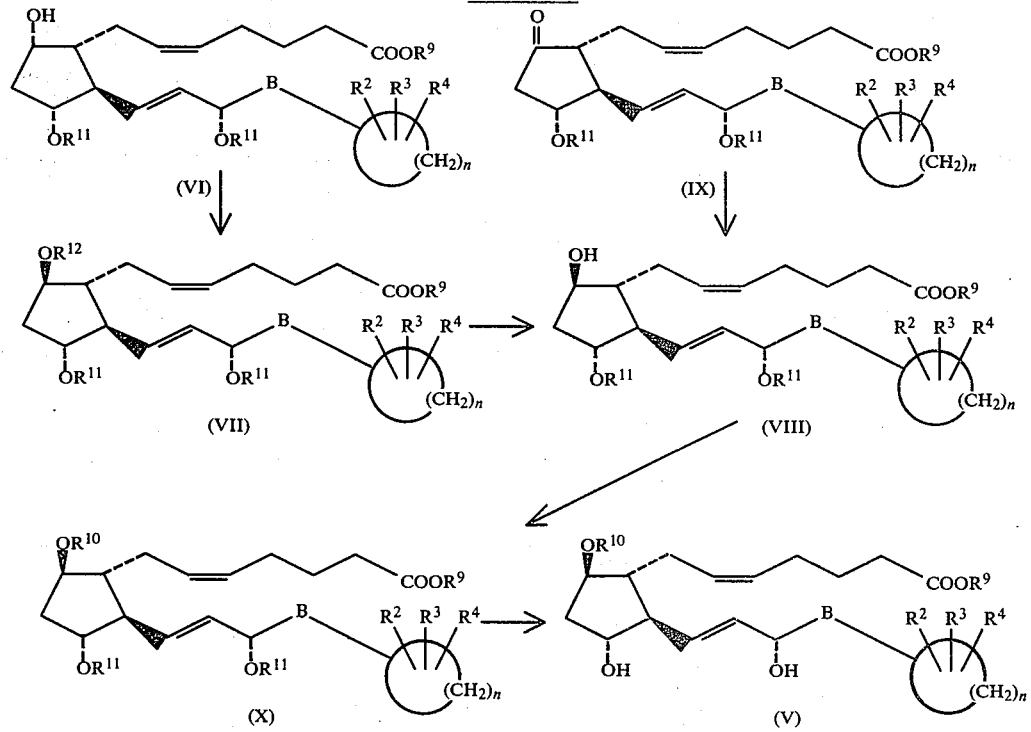

SCHEME A

Referring to Scheme A, compounds of general formula VII may be prepared by reacting a compound of general formula VI with benzoic acid in the presence of triphenylphosphine and diethyl azodicarboxylate in tetrahydrofuran at ambient temperature, and may then be converted into compounds of general formula VIII by hydrolysis under alkaline conditions. The hydrolysis under alkaline conditions may be carried out with an aqueous solution of an alkali metal, e.g. potassium or sodium, hydroxide or carbonate in the presence of a water-miscible solvent such as an ether, e.g. dioxan or to those of general formula V may be carried out by mild hydrolysis under acidic conditions with (1) an aqueous solution of an organic acid such as acetic acid, propionic acid, oxalic acid or p-toluenesulphonic acid, or an aqueous solution of an inorganic acid such as hydrochloric acid, sulphuric acid or phosphoric acid, advantageously in the presence of an inert organic solvent miscible with water, e.g. a lower alkanol such as methanol or ethanol, preferably methanol, or an ether such as 1,2-dimethoxyethane, dioxan or tetrahydrofuran, preferably tetrahydrofuran, at a temperature of ambient to 75° C., preferably at a temperature below 45° C., or (2) an anhydrous solution of an organic acid such as p-toluenesulphonic acid or trifluoroacetic acid in a lower alkanol such as methanol or ethanol at a temperature of 10° to 45° C., or (3) an anhydrous solution of p-toluenesulphonic acid-pyridine complex in a lower alkanol such as methanol or ethanol at a temperature of 10° to 60° C. Advantageously the mild hydrolysis under acidic conditions may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, a mixture of p-toluenesulphonic acid and methanol or a mixture of p-toluenesulphonic acid-pyridine complex and methanol.

Starting materials of general formula VI or IX may be prepared by the methods described in the following patent specifications and applications, or obvious modifications thereof: Japanese Patent Kokai Nos. 50-13364, 50-25549, 50-148339 and 51-68547, Japanese Patent Application No. 52-88919, British Patent Specifications Nos. 1450691, 1464916, 1488141, 1483240 and 1484210, and British Patent Applications Nos. 30072/75 and 18651/76, U.S. Pat. Nos. 3962312, 3966792, 4034003, 4024174, 4045468 and 4087620 and Belgian Patent No. 844256.

According to a further feature of the present invention, the prostaglandin I$_2$ analogues of general formula II, wherein the symbol === represents the single bond, and the other symbols are as hereinbefore defined, i.e. compounds of the general formula:

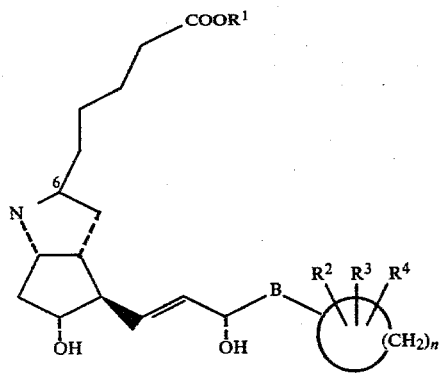

IIB (wherein the absolute configuration of C$_6$ is R or S or a mixture thereof, and the other symbols are as hereinbefore defined) are prepared by reduction of a compound of general formula IIA with a borohydride reducing reagent such as lithium borohydride, potassium borohydride, sodium borohydride, zinc borohydride or sodium cyanoborohydride, in an inert organic solvent such as a lower alkanol, e.g. methanol or ethanol, at a temperature from ambient to −20° C. The product of general formula IIB, thus obtained, is a mixture of isomers in which the absolute configuration of C$_6$ is R and S. If desired, the mixture may be separated by thin layer, column or high-speed liquid chromatography on silica gel to give each of the isomers.

Esters of the PGI$_2$ analogues of general formula II, wherein R$^1$ represents a staight- or branched-chain alkyl group, and the other symbols are as hereinbefore defined, may be prepared by esterification of the corresponding acid of general formula II, wherein R$^1$ represents a hydrogen atom, by methods known per se, for example by reaction with the appropriate diazoalkane in an inert organic solvent, e.g. diethyl ether, ethyl acetate, methylene chloride, acetone or a mixture of two or more of them, at a temperature from ambient to −10° C., preferably 0° C.

Acids of the PGI$_2$ analogues of general formula II, wherein R$^1$ represents a hydrogen atom, and the other symbols are as hereinbefore defined, may be prepared by saponification of the corresponding ester of general formula II, wherein R$^1$ is other than a hydrogen atom, by methods known per se, for example by reaction with an aqueous solution of an alkali metal, e.g. sodium or potassium, or an alkaline earth metal, e.g. calcium or barium, hydroxide or carbonate in the presence of a water-miscible solvent such as an ether, e.g. dioxan or tetrahydrofuran, or a lower alkanol, e.g. methanol or ethanol, at a temperature from −10° to 70° C., preferably ambient temperature.

Compounds of general formula II, wherein R$^1$ represents a hydrogen atom, may, if desired, be converted by methods known per se into salts. Preferably the salts are non-toxic salts. By the term 'non-toxic salts', as used in this specification, is meant salts the cations (or in the case of acid addition salts referred to hereinafter the anions) of which are relatively innocuous to the animal organism when used in therapeutic doses so that the beneficial pharmacological properties of the compounds of general formula II are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, e.g. tetraalkylammonium, such as tetramethylammonium salts, and other organic amine salts such as methylamine salts, dimethylamine salts, cyclopentylamine salts, benzylamine salts, phenylethylamine salts, piperidine salts, monoethanolamine salts, diethanolamine salts, lysine salts and arginine salts.

Salts may be prepared from the acids of general formula II, wherein R$^1$ represents a hydrogen atom, by methods known per se, for example by reaction of stoichiometric quantities of an acid of general formula II and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

The PGI$_2$ analogues of general formula II may, if desired, be converted by methods known per se into acid addition salts, which are preferably non-toxic as hereinbefore defined.

Acid addition salts may be prepared from the compounds of general formula II by methods known per se, for example by reaction of stoichiometric quantities of a compound of general formula II and the appropriate acid, e.g. an inorganic acid such as hydrochloric acid, hydrobromic acid, hydroiodic acid, sulphuric acid, phosphoric acid or nitric acid, or an organic acid such as acetic acid, propionic acid, lactic acid, tartaric acid, citric acid, methanesulphonic acid, ethanesulphonic acid, benzenesulphonic acid, toluenesulphonic acid, isethionic acid or succinic acid, in a suitable solvent. The acid addition salts may be purified by recrystallisation from a suitable solvent or suitable mixture of two or more solvents.

The PGI$_2$ analogues of general formula II and their non-toxic acid addition salts and, when R$^1$ represents a hydrogen atom, their non-toxic salts, possess the valuable pharmacological properties typical of the prostaglandins in a selective fashion, in particular hypotensive activity, inhibitory activity on blood platelet aggregation and stimulatory activity on uterine contraction, and are useful in the treatment of hypertension, in the treatment of disorders of the peripheral circulation, in the prevention and treatment of cerebral thrombosis, myocardial infarction and arteriosclerosis.

For example, in standard laboratory tests, (i) by intravenous administration to the allobarbital-anaesthetized dog, (13E)-(9α,11α,15α)-6,9-nitrilo-11,15-dihydroxy-15-(3-propyl)cyclopentyl-16,17,18,19,20-pentanorprost-13-enoic acid methyl ester produces a fall in blood pressure of 14 mmHg and 36 mmHg lasting 9 and 24 minutes at the doses of 1 and 2 μg/kg animal body weight, respectively, (13E)-(9α,11α,15α)-6,9-nitrilo-11,15-dihydroxy-15-(3-propyl)cyclopentyl-16,17,18,19,20-pentanorprost-13-enoic acid produces a fall in blood pressure of 26 mmHg and 66 mmHg lasting 4 and 12 minutes at the doses of 0.5 and 2 μg/kg animal body weight, respectively, (13E)-(9α,11α,15α)-6,9-nitrilo-11,15-dihydroxy-15-(4-propyl)cyclohexyl-16,17,18,19,20-pentanorprost-13-enoic acid methyl ester produces a fall in blood pressure of 10 mmHg and 42 mmHg lasting 20 and 65 minutes at the doses of 10 and 30 μg/kg animal body weight, respectively, (13E)-(9α,11α,15α)-6,9-nitrilo-11,15-dihydroxy-15-(4-propyl)cyclohexyl-16,17,18,19,20-pentanorprost-13-enoic acid produces a fall in blood pressure of 26 mmHg and 38 mmHg lasting 9 and 11 minutes at the doses of 5 and 10 μg/kg animal body weight, respectively, (13E)-(9α,11α,15α)-6,9-nitrilo-11,15-dihydroxy-15-(3-butyl)cyclopentyl-16,17,18,19,20-pentanorprost-13-enoic acid produces a fall in blood pressure of 22 mmHg and 38 mmHg lasting 9 and 10 minutes at the doses of 1 and 2 μg/kg animal body weight, respectively, and (13E)-(9α,11α,15α)-6,9-nitrilo-11,15-dihydroxy-15-(3-butyl)cyclopentyl-16,17,18,19,20-pentanorprost-13-enoic acid methyl ester produces a fall in blood pressure of 12 mmHg and 32 mmHg lasting 26 and 40 minutes at the doses of 4 and 10 μg/kg animal body weight, respectively, and (ii) (13E)-(6RS,9α,11α,15α)-6,9-imino-11,15-dihydroxy-15-(3-propyl)cyclopentyl-16,17,18,19,20-pentanorprost-13-enoic acid methyl ester, (13E)-(9α,11α,15α)-6,9-nitrilo-11,15-dihydroxy-15-(3-propyl)cyclopentyl-16,17,18,19,20-pentanorprost-13-enoic acid methyl ester, (13E)-(9α,11α,15α)-6,9-nitrilo-11,15-dihydroxy-15-(3-propyl)cyclopentyl-16,17,18,19,20-pentanorprost-13-enoic acid, (13E)-(9α,11α,15α)-6,9-nitrilo-11,15-dihydroxy-15-(4-propyl)cyclohexyl-16,17,18,19,20-pentanorprost-13-enoic acid methyl ester, (13E)-(9α,11α,15α)-6,9-nitrilo-11,15-dihydroxy-15-(4-propyl)cyclohexyl-16,17,18,19,20-pentanorprost-13-enoic acid, (13E)-(9α,11α,15α)-6,9-nitrilo-11,15-dihydroxy-15-(3-butyl)cyclopentyl-16,17,18,19,20-pentanorprost-13-enoic acid and (13E)-(9α,11α,15α)-6,9-nitrilo-11,15-dihydroxy-15-(3-butyl)cyclopentyl-16,17,18,19,20-pentanorprost-13-enoic acid methyl ester produce a 50% inhibition of adenosine diphosphate-induced blood platelet aggregation in platelet-rich plasma of rats at the concentrations of 21.5, $2.07 \times 10^{-2}$, $2.15 \times 10^{-2}$, $9.9 \times 10^{-2}$, $9.5 \times 10^{-2}$, $3.5 \times 10^{-2}$ and $2.8 \times 10^{-2}$ μg/ml, respectively, in comparison with controls.

Preferred PGI$_2$ analogues of the present invention are as follows: (13E)-(9α,11α,15α)-6,9-nitrilo-11,15-dihydroxy-15-cyclobutyl-16,17,18,19,20-pentanorprost-13-enoic acid, (13E)-(9α,11α,15α)-6,9-nitrilo-11,15-dihydroxy-15-(1-propyl)cyclobutyl-16,17,18,19,20-pentanorprost-13-enoic acid, (13E)-(9α,11α,15α)-6,9-nitrilo-11,15-dihydroxy-15-(1-butyl)cyclobutyl-16,17,18,19,20-pentanorprost-13-enoic acid, (13E)-(9α,11α,15α)-6,9-nitrilo-11,15-dihydroxy-15-(1-pentyl)cyclobutyl-16,17,18,19,20-pentanorprost-13-enoic acid, (13E)-(9α,11α,15α)-6,9-nitrilo-11,15-dihydroxy-15-(1-hexyl)cyclobutyl-16,17,18,19,20-pentanorprost-13-enoic acid, (13E)-(9α,11α,15α)-6,9-nitrilo-11,15-dihydroxy-15-(2-methyl)cyclobutyl-16,17,18,19,20-pentanorprost-13-enoic acid, (13E)-(9α,11α,15α)-6,9-nitrilo-11,15-dihydroxy-15-(2-propyl)cyclobutyl-16,17,18,19,20-pentanorprost-13-enoic acid, (13E)-(9α,11α,15α)-6,9-nitrilo-11,15-dihydroxy-15-(3-ethyl)cyclobutyl-16,17,18,19,20-pentanorprost-13-enoic acid, (13E)-(9α,11α,15α)-6,9-nitrilo-11,15-dihydroxy-15-(3-propyl)cyclobutyl-16,17,18,19,20-pentanorprost-13-enoic acid, (13E)-(9α,11α,15α)-6,9-nitrilo-11,15-dihydroxy-15-(2,3,4-triethyl)cyclobutyl-16,17,18,19,20-pentanorprost-13-enoic acid, (13E)-(9α,11α,15α)-6,9-nitrilo-11,15-dihydroxy-15-cyclopentyl-16,17,18,19,20-pentanorprost-13-enoic acid, (13E)-(9α,11α,15α)-6,9-nitrilo-11,15-dihydroxy-16-cyclopentyl-17,18,19,20-tetranorprost-13-enoic acid, (13E)-(9α,11α,15α)-6,9-nitrilo-11,15-dihydroxy-17-cyclopentyl-18,19,20-trinorprost-13-enoic acid, (13E)-(9α,11α,15α)-6,9-nitrilo-11,15-dihydroxy-16-cyclopentyl-18,19,20-trinorprost-13-enoic acid, (13E)-(9α,11α,15α)-6,9-nitrilo-11,15-dihydroxy-18-cyclopentyl-19,20-dinorprost-13-enoic acid, (13E)-(9α,11α,15α)-6,9-nitrilo-11,15-dihydroxy-17-cyclopentyl-19,20-dinorprost-13-enoic acid, (13E)-(9α,11α,15α)-6,9-nitrilo-11,15-dihydroxy-15-(2-pentyl)cyclopentyl-16,17,18,19,20-pentanorprost-13-enoic acid, (13E)-(9α,11α,15α)-6,9-nitrilo-11,15-dihydroxy-15-(2,2-dimethyl)cyclopentyl-16,17,18,19,20-pentanorprost-13-enoic acid, (13E)-(9α,11α,15α)-6,9-nitrilo-11,15-dihydroxy-15-(3-ethyl)cyclopentyl-16,17,18,19,20-pentanorprost-13-enoic acid, (13E)-(9α,11α,15α)-6,9-nitrilo-11,15-dihydroxy-15-(3-propyl)cyclopentyl-16,17,18,19,20-pentanorprost-13-enoic acid, (13E)-(9α,11α,15α)-6,9-nitrilo-11,15-dihydroxy-15-(3-butyl)cyclopentyl-16,17,18,19,20-pentanorprost-13-enoic acid, (13E)-(9α,11α,15α)-6,9-nitrilo-11,15-dihydroxy-15-(3-tert-butyl)cyclopentyl-16,17,18,19,20-pentanorprost-13-enoic acid, (13E)-(9α,11α,15α)-6,9-nitrilo-11,15-dihydroxy-15-(1-methyl-3-propyl)cyclopentyl-16,17,18,19,20-pentanorprost-13-enoic acid, (13E)-(9α,11α,15α)-6,9-nitrilo-11,15-dihydroxy-15-(2-methyl-3-propyl)cyclopentyl-16,17,18,19,20-pentanorprost-13-enoic acid, (13E)-(9α,11α,15α)-6,9-nitrilo-11,15-dihydroxy-15-(2-methyl-4-propyl)cyclopentyl- 16,17,18,19,20-pentanorprost-13-enoic acid, (13E)-(9α,11α,15α)-6,9-nitrilo-11,15-dihydroxy-15-cyclohexyl-16,17,18,19,20-pentanorprost-13-enoic acid, (13E)-(9α,11α,15α)-6,9-nitrilo-11,15-dihydroxy-16-cyclohexyl-17,18,19,20-tetranorprost-13-enoic acid, (13E)-(9α,11α,15α)-6,9-nitrilo-11,15-dihydroxy-17-cyclohexyl-18,19,20-trinorprost-13-enoic acid, (13E)-(9α,11α,15α)-6,9-nitrilo-11,15-dihydroxy-16-cyclohexyl-18,19,20-trinorprost-13-enoic acid, (13E)-(9α,11α,15α)-6,9-nitrilo-11,15-dihydroxy-18-cyclohexyl-19,20-dinorprost-13-enoic acid, (13E)-(9α,11α,15α)-6,9-nitrilo-11,15-dihydroxy-16-methyl-17-cyclohexyl-18,19,20-trinorprost-13-enoic acid, (13E)-(9α,11α,15α)-6,9-nitrilo-11,15-dihydroxy-17-cyclohexyl-19,20-dinorprost-13-enoic acid, (13E)-(9α,11α,15α)-6,9-nitrilo-11,15-11,15-dihydroxy-16-methyl-16-cyclohexyl-18,19,20-trinorprost-13-enoic acid, (13E)-(9α,11α,15α)-6,9-nitrilo-11,15-dihydroxy-19-cyclohexyl-20-norprost-13-enoic acid, (13E)-(9α,11α, 15α)-6,9-nitrilo-11,15-dihydroxy-15-(3-ethyl)cyclohexyl-16,17,18,19,20-pentanorprost-13-enoic acid, (13E)-(9α,11α,15α)-6,9-nitrilo-11,15-dihydroxy-15-(3-isopropyl)cyclohexyl-16,17,18,19,20-pentanorprost-13-enoic acid, (13E)-(9α,11α,15α)-6,9-nitrilo-11,15-dihydroxy-15-(4-methyl)cyclohexyl-16,17,18,19,20-pentanorprost-13-enoic acid, (13E)-(9α,11α,15α)-6,9-nitrilo-11,15-dihydroxy-15-(4-ethyl)cyclohexyl-16,17,18,19,20-pentanorprost-13-enoic acid, (13E)-(9α,11α,15α)-6,9-nitrilo-11,15-dihydroxy-15-(4-propyl)cyclohexyl-16,17,18,19,20-pentanorprost-13-enoic acid, (13E)-(9α,11α,15α)-6,9-nitrilo-11,15-dihydroxy-15-(4-tert-butyl)cyclohexyl-16,17,18,19,20-pentanorprost-13-enoic acid, (13E)-(9α,11α,15α)-6,9-nitrilo-11,15-dihydroxy-15-(2,6-dimethyl)cyclohexyl-16,17,18,19,20-pentanorprost-13-enoic acid, (13E)-(9α,11α,15α)-6,9-nitrilo-11,15-dihydroxy-15-(2,2-dimethyl)cyclohexyl-16,17,18,19,20-pentanorprost-13-enoic acid, (13E)-(9α,11α,15α)-6,9-nitrilo-11,15-dihydroxy-15-(2,6-dimethyl-4-propyl)cyclohexyl-16,17,18,19,20-pentanorprost-13-enoic acid, (13E)-(9α,11α,15α)-6,9-nitrilo-11,15-dihydroxy-16-(1-methyl)cyclohexyl-17,18,19,20-tetranorprost-13-enoic acid, (13E)-(9α,11α,15α)-6,9-nitrilo-11,15-dihydroxy-15-cycloheptyl-16,17,18,19,20-pentanorprost-13-enoic acid, (13E)-(9α,11α,15α)-6,9-nitrilo-11,15-dihydroxy-16-cycloheptyl-17,18,19,20-tetranorprost-13-enoic acid, (13E)-(9α,11α,15α)-6,9-nitrilo-11,15-dihydroxy-17-cycloheptyl-18,19,20-trinorprost-13-enoic acid, (13E)-(9α,11α,15α)-6,9-nitrilo-11,15-dihydroxy-16-cycloheptyl-18,19,20-trinorprost-13-enoic acid and the corresponding PGI₂ analogues of general formula II in which the 6,9-nitrilo group is replaced by the 6,9-imino group, and esters, non-toxic salts and non-toxic acid addition salts thereof.

Particularly preferred PGI₂ analogues of the present invention are the esters (13E)-(9α,11α,15α)-6,9-nitrilo-11,15-dihydroxy-15-(3-propyl)cyclopentyl-16,17,18,19,20-pentanorprost-13-enoic acid methyl ester, (13E)-(9α,11α,15α)-6,9-nitrilo-11,15-dihydroxy-16-cyclopentyl-18,19,20-trinorprost-13-enoic acid methyl ester, (13E)-(9α,11α,15α)-6,9-nitrilo-11,15-dihydroxy-15-cyclohexyl-16,17,18,19,20-pentanorprost-13-enoic acid methyl ester, (13E)-(9α,11α,15α)-6,9-nitrilo-11,15-dihydroxy-15-(4-ethyl)cyclohexyl-16,17,18,19,20-pentanorprost-13-enoic acid methyl ester, (13E)-(9α,11α,15α)-6,9-nitrilo-11,15-dihydroxy-15-(4-propyl)cyclohexyl-16,17,18,19,20-pentanorprost-13-enoic acid methyl ester, (13E)-(9α,11α,15α)-6,9-nitrilo-11,15-dihydroxy-15-(3-butyl)cyclopentyl-16,17,18,19,20-pentanorprost-13-enoic acid methyl ester, and (13E)-(9α,11α,15α)-6,9-imino-11,15-dihydroxy-15-(3-propyl)cyclopentyl-16,17,18,19,20-pentanorprost-13-enoic acid methyl ester and their non-toxic acid addition salts, and the acids (13E)-(9α,11α,15α)-6,9-nitrilo-11,15-dihydroxy-15-(3-propyl)cyclopentyl-16,17,18,19,20-pentanorprost-13-enoic acid, (13E)-(9α,11α,15α)-6,9-nitrilo-11,15-dihydroxy-15-(4-propyl)cyclohexyl-16,17,18,19,20-pentanorprost-13-enoic acid, and (13E)-(9α,11α,15α)-6,9-nitrilo-11,15-dihydroxy-15-(3-butyl)cyclopentyl-16,17,18,19,20-pentanorprost-13-enoic acid, and their non-toxic salts and non-toxic acid addition salts.

The following Reference Examples and Examples illustrate the preparation of prostaglandin I₂ analogues of the present invention. In the Reference Examples and Examples 'TLC', 'IR', 'NMR' and 'MS' represent respectively 'Thin layer chromatography', 'Infrared absorption spectrum', 'Nuclear magnetic resonance spectrum' and 'Mass spectrum'. Where solvent ratios are specified in chromatographic separations, the ratios are by volume: the solvents in parentheses show the developing solvent used. Except when specified otherwise, infrared spectra are recorded by the liquid film method, and nuclear magnetic resonance spectra are recorded in deuterochloroform (CDCl₃) solution. By the expression "50% (v/v) saturated aqueous solution of sodium chloride" is meant a saturated solution to which an equal volume of water has been added.

REFERENCE EXAMPLE 1

(5Z,13E)-(9β,11α,15α)-9-Benzoyloxy-11,15-bis(tetrahydropyran-2-yloxy)-15-(3-propyl)cyclopentyl-16,17,18,19,20-pentanorprosta-5,13-dienoic acid methyl ester To a mixture of 1.04 g of (5Z,13E)-(9α,11α,15α)-9-hydroxy-11,15-bis(tetrahydropyran-2-yloxy)-15-(3-propyl)cyclopentyl-16,17,18,19,20-pentanorprosta-5,13-dienoic acid methyl ester, 709 mg of triphenylphosphine, 329 mg of benzoic acid and 15 ml of tetrahydrofuran, was added dropwise 0.47 ml of diethyl azodicarboxylate, and the mixture was stirred at room temperature for 2 hours. The reaction mixture was diluted with ethyl acetate, washed with 1 N hydrochloric acid, water, a saturated aqueous solution of sodium bicarbonate, water and a saturated aqueous solution of sodium chloride, dried over sodium sulphate, and concentrated under reduced pressure. The residue was purified by column chromatography on silica gel using a mixture of cyclohexane and ethyl acetate (10:1) as eluent to give 989 mg of the title compound having the following physical characteristic:

TLC (cyclohexane:ethyl acetate=4:1): Rf=0.69.

REFERENCE EXAMPLE 2

(5Z,13E)-(9α,11α,15α)-9-Hydroxy-11,15-bis(tetrahydropyran-2-yloxy)-15-(3-propyl)cyclopentyl-16,17,18,19,20-pentanorprosta-5,13-dienoic acid methyl ester A mixture of 989 mg of the 9-benzoyloxy compound, prepared as described in Reference Example 1, 240 mg of potassium carbonate and 10 ml of methanol was stirred at 40° C. for 5 hours. The reaction mixture was diluted with ethyl acetate, washed with 1 N hydrochloric acid, water, a saturated aqueous solution of sodium bicarbonate, water and a saturated aqueous solution of sodium chloride, dried over magnesium sulphate, and concentrated under reduced pressure. The residue was purified by column chromatography on silica gel using a mixture of cyclohexane and ethyl acetate (2:1) as eluent to give 523 mg of the title compound having the following physical characteristic:

TLC (cyclohexane:ethyl acetate=4:1): Rf=0.24.

REFERENCE EXAMPLE 3

(5Z,13E)-(9β,11α,15α)-9-(p-Toluenesulphonyloxy)-11,15-bis(tetrahydropyran-2-yloxy)-15-(3-propyl)cyclopentyl-16,17,18,19,20-pentanorprosta-5,13-dienoic acid methyl ester A mixture of 523 mg of the 9β-hydroxy compound, prepared as described in Reference Example 2, 346 mg of p-toluenesulphonyl chloride and 1.46 ml of pyridine was stirred at room temperature for 17 hours. The reaction mixture was diluted with ethyl acetate, washed with 1N hydrochloric acid, water, a saturated aqueous solution of sodium bicarbonate, a 50% (v/v) saturated aqueous solution of sodium chloride and a saturated aqueous solution of sodium chloride, dried over sodium sulphate, and concentrated under reduced pressure. The residue was purified by column chromatography on silica gel using a mixture of cyclohexane and ethyl acetate (4:1) as eluent to give 638 mg of the title compound having the following physical characteristics:

TLC (benzene:ethyl acetate=4:1) Rf=0.61;
IR:ν=1740, 1600, 980 cm$^{-1}$;
NMR:δ=7.80(2H,d), 7.34(2H,d), 5.62-5.10(4H,m), 4.75-4.50(3H,m), 3.69(3H,s), 2.47(3H,s), 2.30(2H,t);
MS:m/e=544, 372, 172.

REFERENCE EXAMPLE 4

The following compounds were prepared by the same procedure as described in Reference Examples 1, 2 and 3 replacing the (5Z,13E)-(9α,11α,15α)-9-hydroxy-11,15-bis(tetrahydropyran-2-yloxy)-15-(3-propyl)-cyclopentyl-16,17,18,19,20-pentanorprosta-5,13-dienoic acid methyl ester by the indicated starting materials:- (1) (5Z,13E)-(9β,11α,15α)-9-(p-Toluenesulphonyloxy)-11,15-bis(tetrahydropyran-2-yloxy)-16-cyclopentyl-18,19,20-trinorprosta-5,13-dienoic acid methyl ester using as starting material (5Z,13E)-(9α,11α,15α)-9-hydroxy-11,15-bis(tetrahydropyran-2-yloxy)-16-cyclopentyl-18,19,20-trinorprosta-5,13-dienoic acid methyl ester.

TLC (benzene:ethyl acetate=4:1) Rf=0.62;
IR:ν=1740, 1600, 980 cm$^{-1}$;
NMR:δ=7.79(2H,d), 7.33(2H,d), 5.6-5.1(4H,m), 4.80-4.50 (3H,m), 3.68(3H,s), 2.46(3H,s), 2.31(2H,t), 0.88(3H,m);
MS:m/e=530, 358, 172. (2) (5Z,13E)-(9β,11α,15α)-9-(p-Toluenesulphonyloxy)-11,15-bis(tetrahydropyran-2-yloxy)-15-cyclohexyl-16,17,18,19,20-pentanorprosta-5,13-dienoic acid methyl ester using as starting material (5Z,13E)-(9α,11α,15α)-9-hydroxy-11,15-bis(tetrahydropyran-2-yloxy)-15-cyclohexyl-16,17,18,19,20-pentanorprosta-5,13-dienoic acid methyl ester.

TLC (benzene:ethyl acetate=4:1) Rf=0.67;
IR:ν=1740, 1600, 980 cm$^{-1}$;
NMR:δ=7.80(2H,d), 7.34(2H,d), 5.6-5.1(4H,m), 4.77-4.45 (3H,m), 3.70(3H,s), 2.48(3H,s), 2.30(2H,t);
MS:m/e=516, 344, 172. (3) (5Z,13E)-(9β,11α,15α)-9-(p-Toluenesulphonyloxy)-11,15-bis(tetrahydropyran-2-yloxy)-15-(4-ethyl)cyclohexyl-16,17,18,19,20-pentanorprosta-5,13-dienoic acid methyl ester using as starting material (5Z,13E)-(9α,11α,15α)-9-hydroxy-11,15-bis(tetrahydropyran-2-yloxy)-15-(4-ethyl)cyclohexyl-16,17,18,19,20-pentanorprosta-5,13-dienoic acid methyl ester.

TLC (benzene:ethyl acetate=4:1) Rf=0.65;
IR:ν=1740, 1600, 980 cm$^{-1}$;
NMR:δ=7.81(2H,d), 7.35(2H,d), 5.6-5.1(4H,m), 4.80-4.50 (3H,m), 3.69(3H,s), 2.47(3H,s), 2.30(2H,t), 0.85(3H,t);
MS:m/e=544, 372, 172. (4) (5Z,13E)-(9β,11α,15α)-9-(p-Toluenesulphonyloxy)-11,15-bis(tetrahydropyran-2-yloxy)-15-(4-propyl)cyclohexyl-16,17,18,19,20-pentanorprosta-5,13-dienoic acid methyl ester using as starting material (5Z,13E)-(9α,11α,15α)-9-hydroxy-11,15-bis(tetrahydropyran-2-yloxy)-15-(4-propyl)cyclohexyl-16,17,18,19,20-pentanorprosta-5,13-dienoic acid methyl ester.

TLC (cyclohexane:ethyl acetate=1:1) Rf=0.67;
IR:ν=2970, 2950, 1745, 1605 cm$^{-1}$;
NMR:δ=7.36(4H,q), 5.5-5.0(4H,m), 4.6-4.3(2H,m), 3.51(3H,s), 2.36(3H,s). (5) (5Z,13E)-(9β,11α,15α)-9-(p-Toluenesulphonyloxy)-11,15-bis(tetrahydropyran-2-yloxy)-15-(3-butyl)cyclopentyl-16,17,18,19,20-pentanorprosta-5,13-dienoic acid methyl ester using as starting material (5Z,13E)-(9α,11α,15α)-9-hydroxy-11,15-bis(tetrahydropyran-2-yloxy)-15-(3-butyl)cyclopentyl-16,17,18,19,20-pentanorprosta-5,13-dienoic acid methyl ester.

TLC (cyclohexane:ethyl acetate=3:1) Rf=0.49;
IR:ν=1600, 1500 cm$^1$.

REFERENCE EXAMPLE 5

(5Z,13E)-(9β,11α,15α)-9-(p-Toluenesulphonyloxy)-11,15-dihydroxy-15-(3-propyl)cyclopentyl-16,17,18,19,20-pentanorprosta-5,13-dienoic acid methyl ester A mixture of 300 mg of the 11,15-bis(tetrahydropyran-2-yloxy) compound prepared as described in Reference Example 3, 10 mg of p-toluenesulphonic acid-pyridine complex and 4 ml of methanol was stirred at 50° C. for one hour. The reaction mixture was diluted with ethyl acetate, washed with water, a 50% (v/v) saturated aqueous solution of sodium chloride and a saturated aqueous solution of sodium chloride, dried over sodium sulphate, and concentrated under reduced pressure. The residue was purified by column chromatography on silica gel using a mixture of cyclohexane and ethyl acetate (1:1) as eluent to give 198 mg of the title compound having the following physical characteristics:

TLC (benzene:ethyl acetate=1:1) Rf=0.50;
IR:ν=3400, 1740, 1600, 980 cm$^{-1}$;
NMR:δ=7.78(2H,d), 7.34(2H,d), 5.54-5.10(4H,m), 4.69-4.48(1H,m), 3.68(3H,s), 2.46(3H,s), 2.29(2H,t);
MS:m/e=372, 354, 172.

The following compounds were prepared from the corresponding 11,15-bis(tetrahydropyran-2-yloxy) compounds, prepared as described in Reference Example 4, by the same procedure as described above:

(1) (5Z,13E)-(9β,11α,15α)-9-(p-Toluenesulphonyloxy)-11,15,-dihydroxy-16-cyclopentyl-18,19,20-trinorprosta-5,13-dienoic acid methyl ester from the product of Reference Example 4(1):

TLC (benzene:ethyl acetate=1:1) Rf=0.52;
IR:ν=3400, 1740, 1600, 980 cm$^{-1}$;
NMR:δ=7.77(2H,d), 7.33(2H,d), 5.6-5.1(4H,m), 4.68-4.48 (1H,m), 3.67(3H,s), 2.45(3H,s), 2.30(2H,t), 0.87(3H,m).

(2) (5Z,13E)-(9β,11α,15α)-9-(p-Toluenesulphonyloxy)-11,15-dihydroxy-15-cyclohexyl-16,17,18,19,20-pentanorprosta-5,13-dienoic acid methyl ester from the product of Reference Example 4(2):

TLC (benzene:ethyl acetate=1:1) Rf=0.57;
IR:ν=3400, 1740, 1600, 980 cm$^{-1}$;
NMR:δ=7.78(2H,d), 7.34(2H,d), 5.6-5.1(4H,m), 4.70-4.50 (1H,m), 3.69(3H,s), 2.47(3H,s), 2.29(2H,t);
MS:m/e=344, 326, 172.

(3) (5Z,13E)-(9β,11α,15α)-9-(p-Toluenesulphonyloxy)-11,15-dihydroxy-15-(4-ethyl)cyclohexyl-16,17,18,19,20-pentanorprosta-5,13-dienoic acid methyl ester from the product of Reference Example 4(3):

TLC (benzene:ethyl acetate=1:1) Rf=0.55;
IR:ν=3400, 1740, 1600, 980 cm$^{-1}$;
NMR:δ=7.79(2H,d), 7.35(2H,d), 5.6-5.1(4H,m), 4.69-4.50 (1H,m), 3.68(3H,s), 2.46(3H,s), 2.29(2H,t), 0.84(3H,t).

(4) (5Z,13E)-(9β,11α,15α)-9-(p-Toluenesulphonyloxy)-11,15-dihydroxy-15-(4-propyl)cyclohexyl-16,17,18,19,20-pentanorprosta-5,13-dienoic acid methyl ester from the product of Reference Example 4(4):

TLC (ethyl acetate:cyclohexane=1:1) Rf=0.24;
IR:ν=2970, 2950, 2870, 1745, 1605 cm$^{-1}$;
NMR:δ=7.36(4H,q), 5.5-5.0(4H,m), 3.51(3H,s), 2.33(3H,s);
MS:m/e=386, 368, 325, 271, 172, 91.

(5) (5Z,13E)-(9β,11α,15α)-9-(p-Toluenesulphonyloxy)-11,15-dihydroxy-15-(3-butyl)cyclopentyl-16,17,18,19,20-pentanorprosta-5,13-dienoic acid methyl ester from the product of Reference Example 4(5):

TLC (ethyl acetate:cyclohexane=1:1) Rf=0.10;
IR:ν=3400, 3020, 2970, 2940, 2870, 1745, 1601, 1500, 1440, 1370, 1190, 1180, 1100, 980, 890 cm$^{-1}$;
NMR:δ=7.7(2H,d), 7.3(2H,d), 5.7-5.0(4H,m), 4.8-4.3(1H,m), 4.3.-3.3(2H,m), 3.7(3H,s), 2.4(3H,s), 1.1-0.5(3H,t);
MS:m/e=386, 368, 355, 342, 337, 329, 311, 285, 245, 227, 205, 91.

EXAMPLE 1

(5Z,13E)-(9β,11α,15α)-9-Azido-11,15-dihydroxy-15-(3-propyl)cyclopentyl-16,17,18,19,20-pentanorprosta-5,13-dienoic acid methyl ester A mixture of 182 mg of the title 9-(p-toluenesulphonyloxy) compound, prepared as described in Reference Example 5, 43 mg of sodium azide and 3 ml of dimethyl sulphoxide was stirred at 50°-55° C. for two hours. The reaction mixture was diluted with ethyl acetate, washed with water and a saturated aqueous solution of sodium chloride, dried over sodium sulphate and concentrated under reduced pressure. The residue was purified by column chromatography on silica gel using a mixture of cyclohexane and ethyl acetate (1:2) as eluent to give 113 mg of the title compound having the following physical characteristics:

TLC (benzene:ethyl acetate=1:2) Rf=0.42;
IR:ν=3380, 2120, 1745, 980 cm$^{-1}$;
NMR:δ=5.60-5.20(4H,m), 4.03-3.74(3H,m), 3.67(3H,s), 2.32(2H,t).

The following compounds were prepared from the corresponding 9-(p-toluenesulphonyloxy) compounds prepared as described in Reference Example 5, by the same procedure as described above.

(1) (5Z,13E)-(9β,11α, 15α)-9-Azido-11,15-dihydroxy-16-cyclopentyl-18,19,20-trinorprosta-5,13-dienoic acid methyl ester from the product of Reference Example 5(1):

TLC (benzene:ethyl acetate=1:2) Rf=0.43;
IR:ν=3400, 2120, 1740, 980 cm$^{-1}$;
NMR:δ=5.57-5.13(4H,m), 4.10-3.75(3H,m), 3.66(3H,s), 2.33(2H,t), 0.87(3H,m).

(2) (5Z,13E)-(9β,11α,15α)-9-Azido-11,15-dihydroxy-15-cyclohexyl-16,17,18,19,20-pentanorprosta-5,13-dienoic acid methyl ester from the product of Reference Example 5(2):

TLC (benzene:ethyl acetate=1:2) Rf=0.48;
IR:ν=3400, 2120, 1745, 980 cm$^{-1}$;
NMR:δ=5.62-5.18(4H,m), 4.05-3.78(3H,m), 3.68(3H,s), 2.31(2H,t).

(3) (5Z,13E)-(9β,11α,15α)-9-Azido-11,15-dihydroxy-15-(4-ethyl)cyclohexyl-16,17,18,19,20-pentanorprosta-5,13-dienoic acid methyl ester from the product of Reference Example 5(3):

TLC (benzene:ethyl acetate=1:2) Rf=0.45;
IR:ν=3400, 2120, 1740, 980 cm$^{-1}$;
NMR:δ=5.55-5.10(4H,m), 4.12-3.76(3H,m), 3.67(3H,s), 2.32(2H,t), 0.86(3H,t).

(4) (5Z,13E)-(9α,11α,15α)-9-Azido-11,15-dihydroxy-15-(4-propyl)cyclohexyl-16,17,18,19,20-pentanorprosta-5,13-dienoic acid methyl ester from the product of Reference Example 5(4):

TLC (ethyl acetate:methanol=9:1) Rf=0.46;
IR:ν=2970, 2950, 2880, 2130, 1750 cm$^{-1}$;
NMR:δ=5.54-5.00(4H,m), 3.51(3H,s);
MS:m/e=419, 402, 401, 390, 388, 376, 357, 346, 332, 294, 266, 264.

(5) (5Z,13E)-(9α,11α,15α)-9-Azido-11,15-dihydroxy-15-(3-butyl)cyclopentyl-16,17,18,19,20-pentanorprosta-5,13-dienoic acid methyl ester from the product of Reference Example 5(5):

TLC (ethyl acetate:cyclohexane=3:1) Rf=0.51;
IR:ν=3400, 3050, 2950, 2870, 2120, 1745, 1650, 1440, 1250, 970 cm$^{-1}$;
NMR:δ=6.0-5.0(4H,m), 4.5-3.5(3H,m), 3.7(3H,s), 1.1-0.6(3H,t);
MS:m/e=419, 401, 398, 319, 294.

EXAMPLE 2

(13E)-(9α,11α,15α)-6,9-Nitrilo-11,15-dihydroxy-15-(3-propyl)cyclopentyl-16,17,18,19,20-pentanorprost-13-enoic acid methyl ester A mixture of 100 mg of the 9-azido compound, prepared as described in Example 1, and 2 ml of toluene was stirred at 55°-60° C. for 20 hours. The reaction mixture was purified by column chromatography on silica gel using a mixture of ethyl acetate and methanol (9:1) as eluent to give 81 mg of the title compound having the following physical characteristics:

TLC (ethyl acetate:methanol=3:1) Rf=0.70;
IR:ν=3380, 1745, 1640, 980 cm$^{-1}$;
NMR:δ=5.61-5.45(2H,m), 4.54-4.24(1H,m), 3.97-3.40(4H,m), 3.70(3H,s);
MS:m/e=405, 387, 374, 369, 332, 318, 305, 294.

The following compounds were prepared from the corresponding 9-azido compounds, prepared as described in Example 1, by the same procedure as described above.

(1) (13E)-(9α,11α,15α)-6,9-Nitrilo-11,15-dihydroxy-16-cyclopentyl-18,19,20-trinorprost-13-enoic acid methyl ester from the product of Example 1(1):

TLC (ethyl acetate:methanol=3:1) Rf=0.72;
IR:ν=3380, 1745, 1640, 980 cm$^{-1}$;
NMR:δ=5.63-5.42(2H,m), 4.55-4.25(1H,m), 4.00-3.41(2H,m), 3.68(3H,s), 0.89(3H,m);
MS:m/e=391, 373, 360, 355, 318, 304, 291, 280.

(2) (13E)-(9α,11α,15α)-6,9-Nitrilo-11,15-dihydroxy-15-cyclohexyl-16,17,18,19,20-pentanorprost-13-enoic acid methyl ester from the product of Example 1(2):

TLC (ethyl acetate:methanol=3:1) Rf=0.78;
IR:$\nu$=3380, 1745, 1640, 980 cm$^{-1}$;
NMR:$\delta$=5.65–5.47(2H,m), 4.51–4.21(1H,m), 4.02–3.45(2H,m), 3.69(3H,s);
MS:m/e=377, 359, 346, 341, 304, 290, 277, 266.

(3) (13E)-(9α,11α,15α)-6,9-Nitrilo-11,15-dihydroxy-15-(4-ethyl)cyclohexyl-16,17,18,19,20-pentanorprost-13-enoic acid methyl ester from the product of Example 1(3):

TLC (ethyl acetate:methanol=3:1) Rf=0.76;
IR:$\nu$=3380, 1745, 1640, 980 cm$^{-1}$; NMR: $\delta$=5.60–5.43(2H,m), 4.52–4.23(1H,m), 4.00–3.40(2H,m), 3.70(3H,s), 0.88(3H,t);
MS: m/e=405, 387, 374, 369, 332, 318, 305, 294.

(4) (13E)-(9α,11α,15α)-6,9-Nitrilo-11,15-dihydroxy-15-(4-propyl)cyclohexyl-16,17,18,19,20-pentanorprost-13-enoic acid methyl ester from the product of Example 1(4): TLC (ethyl acetate:methanol=7:3) Rf=0.50; IR:$\nu$=2970, 2950, 2870, 1745, 1640, 1440 cm$^{-1}$; NMR: $\delta$=5.58–5.35(2H,m), 4.5–4.1(1H,m), 3.66(3H,s), 3.9–3.5(2H,m);
MS: m/e=402, 401, 390, 388, 376, 357, 346, 332, 294, 266, 264.

(5) (13E)-(9α,11α,15α)-6,9-Nitrilo-11,15-dihydroxy-15-(3-butyl)cyclopentyl-16,17,18,19,20-pentanorprost-13-enoic acid methyl ester from the product of Example 1(5):

TLC (ethyl acetate:methanol=9:1) Rf=0.16; IR:$\nu$=3350, 2950, 2870, 1745, 1640, 1440, 1090, 970 cm$^{-1}$; NMR:$\delta$=5.6–5.4(2H,m), 4.5–4.1(1H,m), 4.0–3.5(2H,m), 3.66(3H,s), 1.0–0.7(3H,t);
MS: m/e=419, 401, 388, 319, 294.

EXAMPLE 3

(13E)-(9α,11α,15α)-6,9-Nitrilo-11,15-dihydroxy-15-(3-propyl)cyclopentyl-16,17,18,19,20-pentanorprost-13-enoic acid A mixture of 74 mg of the methyl ester, prepared as described in Example 2, 0.40 ml of 0.5N aqueous sodium hydroxide and 1.5 ml of methanol was stirred at 35° C.–40° C. for 3.5 hours. The reaction mixture was concentrated under reduced pressure. The residue was dissolved in water, washed with diethyl ether, and the aqueous layer was neutralized with 0.349 ml of 0.5N hydrochloric acid, and then concentrated under reduced pressure. The residue was dissolved in isopropanol, filtered, and the filtrate was concentrated under reduced pressure to give 67 mg of the title compound having the following physical characteristics:

TLC (methanol:ethyl acetate=1:1) Rf=0.34;
IR:$\nu$=3350, 1720, 1645, 980 cm$^{-1}$;
NMR:$\delta$=6.00–5.38(5H,m), 4.63–4.34(1H,m), 4.04–3.73(2H,m).

The following compounds were prepared from the corresponding methyl ester, prepared as described in Example 2, by the same procedure as described above.

(1) (13E)-(9α,11α,15α)-6,9-Nitrilo-11,15-dihydroxy-15-(4-propyl)cyclohexyl-16,17,18,19,20-pentanorprost-13-enoic acid from the product of Example 2(4):

TLC (methanol:ethyl acetate=1:1) Rf=0.32;
IR:$\nu$=2980, 2950, 2880, 1720, 1645, 1575 cm$^{-1}$;
NMR:$\delta$=5.60–5.37(2H,m), 4.6–3.5(3H,m);
MS:m/e=405, 387, 376, 362, 319, 280.

(2) (13E)-(9α,11α,15α)-6,9-Nitrilo-11,15-dihydroxy-15-(3-butyl)cyclopentyl-16,17,18,19,20-pentanorprost-13-enoic acid from the product of Example 2(5): TLC (methanol:ethyl acetate=1:1) Rf=0.37;
IR:$\nu$=3450, 2950, 2870, 2500, 1720, 1640, 1570, 1090, 1040, 970 cm$^{-1}$;
NMR: (CD$_3$OD solution): $\delta$=5.7–5.4(2H,m), 4.7–4.2(1H,m), 4.0–3.6(2H,m), 1.0–0.7(3H,t);
MS: m/e=405, 387, 369, 319, 280, 262, 244, 162.

EXAMPLE 4

(13E)-(9α,11α,15α)-6,9-Imino-11,15-dihydroxy-15-(3-propyl)cyclopentyl-16,17,18,19,20-pentanorprost-13-enoic acid methyl ester A mixture of 19 mg of the 6,9-nitrilo compound, prepared as described in Example 2, 8.8 mg of sodium borohydride and 1 ml of methanol was stirred at ambient temperature for 10 minutes, and water was then added. The mixture was stirred at ambient temperature for 20 minutes, and extracted with chloroform. The extract was dried over magnesium sulphate, and concentrated under reduced pressure. The residue was purified by recrystallisation with a mixture of ethyl acetate and hexane to give 5 mg of the title compound having the following physical characteristics:

TLC (methanol) Rf=0.15;
IR:$\nu$=3350, 1745, 980 cm$^{-1}$;
NMR:$\delta$=5.61–5.40(2H,m), 4.00–3.55(5H,m), 3.67(3H,s), 2.62(3H,bs), 2.32(2H,t).

The present invention includes within its scope pharmaceutical compositions which comprise at least one new therapeutically useful compound of general formula II or non-toxic acid addition salt thereof or, when R$^1$ in formula II represents a hydrogen atom, non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, alginic acid, lactose or mannitol. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, each dose per person is generally between 0.05 and 500 μg by parenteral administration in the treatment of hypertension or disorders of the peripheral circulation, and between 0.05 and 500 μg by parenteral administration in the prevention and treatment of cerebral thrombosis, myocardial infarction and arteriosclerosis.

The following Example illustrates pharmaceutical compositions according to the invention.

EXAMPLE 5

(13E)-(9α,11α,15α)-6,9-Nitrilo-11,15-dihydroxy-15-(3-propyl)cyclopentyl-16,17,18,19,20-pentanorprost-13-enoic acid methyl ester (500 μg) was dissolved in ethanol (5 ml). The solution was then sterilised by passage through a bacteria-retaining filter and placed in 0.1 ml portions in 1 ml ampoules, to give 10 μg of (13E)-(9α,11α,15α)-6,9-nitrilo-11,15-dihydroxy-15-(3-propyl)cyclopentyl-16,17,18,19,20-pentanorprost-13-enoic acid methyl ester per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin I₂ analogue of the formula:

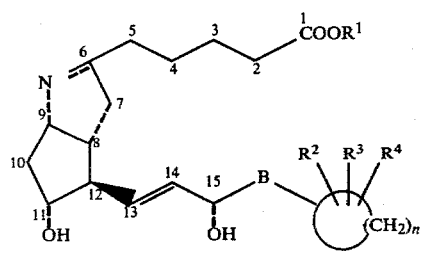

wherein $R^1$ represents a hydrogen atom, a straight- or branched-chain alkyl group of from 1 to 12 carbon atoms, a carbocyclic aralkyl group of from 7 to 12 carbon atoms, a cycloalkyl group of from 4 to 7 carbon atoms unsubstituted or substituted by at least one straight- or branched-chain alkyl group of from 1 to 4 carbon atoms, a phenyl group unsubstituted or substituted by chlorine, trifluoromethyl, straight- or branched-chain alkyl of from 1 to 4 carbon atoms, or phenyl, or represents a group $-C_pH_{2p}COOR^5$, $-C_qH_{2q}OR^6$ or

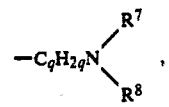

wherein $R^5$, $R^7$ and $R^8$, which may be the same or different, each represent a straight- or branched-chain alkyl group of from 1 to 4 carbon atoms, $R^6$ represents a hydrogen atom or a straight- or branched-chain alkyl group of from 1 to 4 carbon atoms, p represent an integer of from 1 to 12, and q represents an integer of from 2 to 12, $R^2$, $R^3$ and $R^4$, which may be the same or different, each represent a hydrogen atom or a straight- or branched-chain alkyl group of from 1 to 8 carbon atoms, B represents a single bond, or a straight- or branched-chain alkylene group of from 1 to 4 carbon atoms, n represents 3, 4, 5 or 6, the symbol ═ attached to the C₆ carbon atom represents a single or double bond, the double bond between C₁₃–C₁₄ is trans, and the hydroxy groups attached to the C₁₁ to C₁₅ carbon atoms of formula II are in α-configuration, and non-toxic acid addition salts thereof and, when $R^1$ represents a hydrogen atom, non-toxic salts thereof.

2. A prostaglandin analogue according to claim 1 wherein $R^1$ represents a hydrogen atom or a straight- or branched-chain alkyl group of from 1 to 4 carbon atoms.

3. A prostaglandin analogue according to claim 1 wherein $R^1$ represents a hydrogen atom or a methyl group.

4. A prostaglandin analogoue according to claim 1 wherein B represents a single bond or a methylene group.

5. A prostaglandin analogue according to claim 1 wherein n represents 4 or 5.

6. A prostaglandin analogue according to claim 1 wherein one of the substituents $R^2$, $R^3$ and $R^4$ represents a straight- or branched-chain alkyl group of from 1 to 4 carbon atoms and the other two substituents represent hydrogen atoms.

7. A porstaglandin analogue according to claim 1 wherein the group

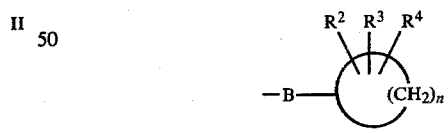

represents 3-propylcyclopentyl, 1-cyclopentylethyl, cyclohexyl, 4-ethylcyclohexyl, 4-propylcyclohexyl or 3-butylcyclopentyl.

8. A prostaglandin analogue according to claim 1 which is (13E)-(9α,11α,15α)-6,9-nitrilo-11,15-dihydroxy-15-(3-propyl)cyclopentyl-16,17,18,19,20-pentanorprost-13-enoic acid methyl ester and non-toxic acid addition salts thereof.

9. A prostaglandin analogue according to claim 1 which is (13E)-(9α,11α,15α)-6,9-nitrilo-11,15-dihydroxy-16-cyclopentyl-18,19,20-trinorprost-13-enoic acid methyl ester and non-toxic acid addition salts thereof.

10. A prostaglandin analogue according to claim 1 which is (13E)-(9α,11α,15α)-6,9-nitrilo-11,15-dihydroxy-15-cyclohexyl-16,17,18,19,20-pentanorprost-13-enoic acid methyl ester and non-toxic acid addition salts thereof.

11. A prostaglandin analogue according to claim 1 which is (13E)-(9α,11α15α)-6,9-nitrilo-11,15-dihydroxy-15-(4-ethyl)cyclohexyl-16,17,18,19,20-pentanorprost-13-enoic acid methyl ester and non-toxic acid addition salts thereof.

12. A prostaglandin analogue according to claim 1 which is (13E)-(9α,11α,15α)-6,9-nitrilo-11,15-dihydroxy-15-(4-propyl)cyclohexyl-16,17,18,19,20-pentanorprost-13-enoic acid methyl ester and non-toxic acid addition salts thereof.

13. A prostaglandin analogue according to claim 1 which is (13E)-(9α,11α,15α)-6,9-nitrilo-11,15-dihydroxy-15-(3-butyl)cyclopentyl-16,17,18,19,20-pentanorprost-13-enoic acid methyl ester and non-toxic acid addition salts thereof.

14. A prostaglandin analogue according to claim 1 which is (13E)-(9α,11α,15α)-6,9-nitrilo-11,15-dihydroxy-15-(3-propyl)cyclopentyl-16,17,18,19,20-pentanorprost-13-enoic acid and non-toxic salts and acid addition salts thereof.

15. A prostaglandin analogue according to claim 1 which is (13E)-(9α,11α,15α)-6,9-nitrilo-11,15-dihydroxy-15-(4-propyl)cyclohexyl-16,17,18,19,20-pentanorprost-13-enoic acid and non-toxic salts and acid addition salts thereof.

16. A prostaglandin analogue according to claim 1 which is (13E)-(9α,11α,15α)-6,9-nitrilo-11,15-dihydroxy-15-(3-butyl)cyclopentyl-16,17,18,19,20-pentanorprost-13-enoic acid and non-toxic salts and acid addition salts thereof.

17. A prostaglandin analogue according to claim 1 which is (13E)-(9α,11α,15α)-6,9-imino-11,15-dihydroxy-15-(3-propyl)cyclopentyl-16,17,18,19,20-pentanorprost-13-enoic acid methyl ester and non-toxic acid addition salts thereof.

18. Compounds of the general formula:

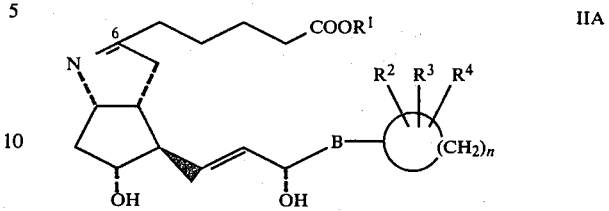

wherein the various symbols are as defined in claim 1.

19. A pharmaceutical composition useful in the treatment of hypertension, in the treatment of disorders of the peripheral circulation, and in the prevention and treatment of cerebral thrombosis, myocardial infarction and arteriosclero which comprises, as active ingredient, an effective amount of a prostaglandin analogue as claimed in any one of claims 2 to 17 or 1 or a non-toxic acid addition salt thereof or, when $R^1$ in general formula II represents a hydrogen atom, a non-toxic salt thereof, in association with a pharmaceutical carrier or coating.

20. A pharmaceutical composition useful in the treatment of hypertension, in the treatment of disorders of the peripheral circulation and in the prevention and treatment of cerebral thrombosis, myocardial infarction and arteriosclerosis, which comprises, as active ingredient, an effective amount of a prostaglandin analogue as claimed in any one of claims 8 to 17 or a non-toxic acid addition salt thereof, or a non-toxic salt of a prostaglandin analogue selected from (13E)-(9α, 11α,15α)-6, 9-nitrilo-11, 15-dihydroxy-15-(3-propyl) cyclopentyl-16, 17, 18, 19, 20-pentanorprost-13-enoic acid, (13E)-(9α,11α,15α) -6,9-nitrilo-11, 15-dihydroxy-15-(4-propyl) cyclohexyl-16, 17, 18, 19, 20-pentanorprost-13-enoic acid, or (13E)-(9α,11α,15α)-6, 9-nitrilo -11, 15-dihydroxy -15-(3-butyl) cyclopentyl-16, 17, 18, 19, 20-pentanorprost-13-enoic acid.

* * * * *